United States Patent
Brandon

[11] Patent Number: 6,019,738
[45] Date of Patent: Feb. 1, 2000

[54] POSTURAL AWARENESS DEVICE

[76] Inventor: Lee Brandon, 7895 Santa Monica Blvd., Suite 109-508, Los Angeles, Calif. 90046

[21] Appl. No.: 09/023,038

[22] Filed: Feb. 13, 1998

[51] Int. Cl.[7] .............................. A61B 5/05; A61B 5/103; A61F 5/00; G08B 23/00
[52] U.S. Cl. ........................ 600/587; 600/594; 128/845; 482/142; 340/573.7
[58] Field of Search ................................... 482/142, 148; 5/621, 630, 636, 637, 638, 640, 922, 940; 600/587, 594; 297/284.4, 284.7; 340/573.1, 573.7; 128/845

[56] References Cited

U.S. PATENT DOCUMENTS

| | | |
|---|---|---|
| 1,904,039 | 8/1933 | Brudu . |
| 2,742,036 | 2/1956 | Montesano . |
| 2,780,693 | 2/1957 | McClellan . |
| 3,042,025 | 7/1962 | Jackson . |
| 3,325,799 | 6/1967 | Farris ..................................... 340/573.1 |
| 3,582,935 | 6/1971 | Verhaeghe . |
| 3,608,541 | 9/1971 | Hall . |
| 3,981,032 | 9/1976 | Brooks . |
| 4,108,164 | 8/1978 | Hall, Sr. . |
| 4,326,506 | 4/1982 | Kawabeta . |
| 4,592,345 | 6/1986 | Wahl . |
| 4,617,525 | 10/1986 | Lloyd ..................................... 340/573.1 |
| 4,730,625 | 3/1988 | Fraser et al. . |
| 4,762,134 | 8/1988 | Gala ......................................... 600/594 |
| 4,858,620 | 8/1989 | Sugarman ............................... 600/587 |
| 5,146,929 | 9/1992 | Sawhill . |
| 5,163,195 | 11/1992 | Hill ............................................. 5/627 |
| 5,279,310 | 1/1994 | Hsien ..................................... 128/845 |
| 5,343,876 | 9/1994 | Rogers ................................ 600/587 X |
| 5,469,841 | 11/1995 | Piscopo . |
| 5,515,865 | 5/1996 | Scanlon ............................... 600/587 X |
| 5,522,401 | 6/1996 | Brucker . |
| 5,545,125 | 8/1996 | Tseng . |
| 5,643,239 | 7/1997 | Solomonow et al. . |
| 5,713,841 | 2/1998 | Graham ............................... 128/845 X |

OTHER PUBLICATIONS

Body–Rite Internet document www.body–rite.com, advertisement for Body Rite, printed Apr. 22, 1997.
Clear Sky Products Internet document www.clearskyprod.com, advertisement for Spine Tuner, printed Apr. 22, 1997.

Primary Examiner—Stephen R. Crow
Assistant Examiner—William LaMarca
Attorney, Agent, or Firm—Michael M. Gerardi

[57] ABSTRACT

An exercise apparatus includes a pad, a signal generating element and an element for detecting a weight applied to the pad and activating the signal generating element when the weight so detected exceeds a predetermined weight.

22 Claims, 4 Drawing Sheets 6,019,738

POSTURAL AWARENESS DEVICE

FIELD OF THE INVENTION

The present invention relates to devices for strengthening the lower back, low abdomen and posture on multiple planes, and for teaching a neutral spine.

BACKGROUND OF THE INVENTION

Devices for monitoring, controlling and correcting posture are described, for example, in U.S. Pat. No. 3,582,935, to Verhaeghe; U.S. Pat. No. 3,981,032, to Brooks; U.S. Pat. No. 4,730,625, to Fraser et al.; U.S. Pat. No. 5,146,929, to Sawhill; U.S. Pat. No. 5,279,310, to Hsien; and U.S. Pat. No. 5,522,401, to Brucker. However, such corrective devices are not designed specifically for use in strengthening the low abdomen and lower back of the user.

A need exists for an apparatus that is useful in an exercise regimen for strengthening the low abdomen and lower back of a human. A need also exists for an apparatus that informs the user when the neutral spine position is maintained during exercise in multiple positions (e.g., sitting, lying, standing).

SUMMARY OF THE PREFERRED EMBODIMENTS

In accordance with one aspect of the present invention, there is provided an apparatus including a pad, signal means and detection means. The signal means is affixed to the pad, and the detection means detects a weight applied to the pad and activates the signal means when the weight so detected exceeds a predetermined weight.

In preferred embodiments, the signal means produces a vibratory signal, an auditory signal or a visible signal. More preferably, the signal means produces a vibratory signal and includes at least one vibrator unit.

According to another preferred embodiment, the inventive apparatus includes a head rest affixed to the pad, preferably detachably affixed to the pad and spaced from the signal means. Preferably the head rest includes a plurality of handles.

According to a more specific embodiment, the inventive apparatus includes a a wedge for insertion between the head rest and the pad.

In another preferred embodiment, the detection means includes a mechanical switch which closes when a weight applied thereto exceeds a predetermined pressure. According to an alternative preferred embodiment, the detection means includes a pressure sensor and an electronic circuit which generates an output when pressure measured by the pressure sensor exceeds a predetermined pressure.

In accordance with another aspect of the present invention, there is provided a method of strengthening the abdomen and lower back of a human by use of an apparatus as described herein.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

BRIEF DESCRIPTION OF THE DRAWINGS

The invention may be more readily understood by referring to the accompanying drawings in which.

Like numerals refer to like parts throughout the several views of the drawings.

DETAILED DESCRIPTION OF THE PREFERRED EMBODIMENTS

The present invention provides devices and methods for strengthening the lower back and low abdomen, and for teaching the user to maintain a neutral spine. By "neutral spine" is meant a biomechanically correct spinal position in which muscular balance is maintained. Neutral spine positions vary with the posture of the user; for example, the neutral spine position of a user with kyphosis will differ from the neutral spine position of a user having a normal posture.

Figure 1A:
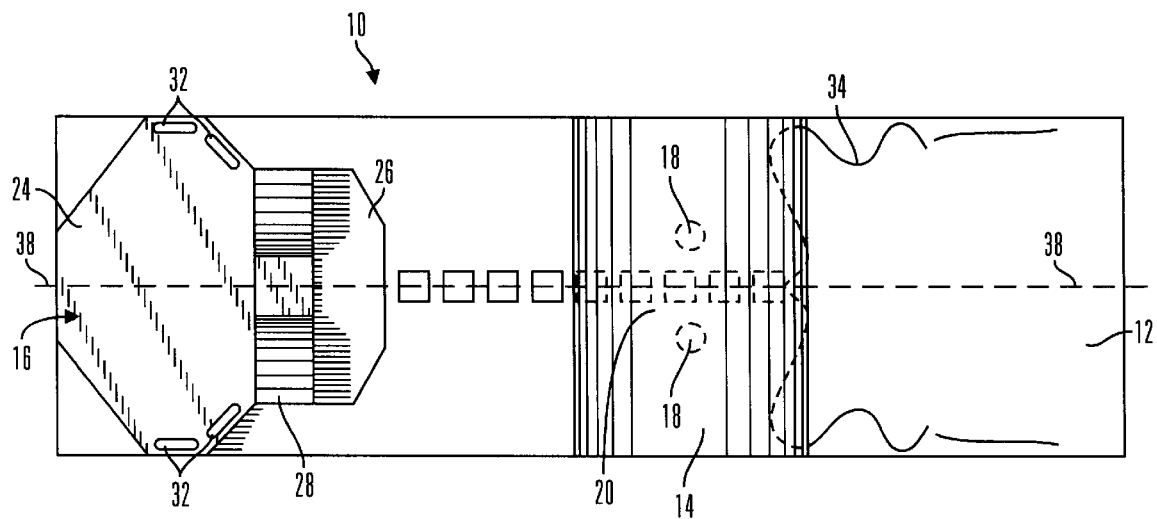
FIGS. 1a–b are top plan and exploded side views, respectively, of a first embodiment employing a detachable head rest and a lumbar pad, with vibrator units and pressure sensors disposed within the lumbar unit shown in phantom.
Figure 1B:
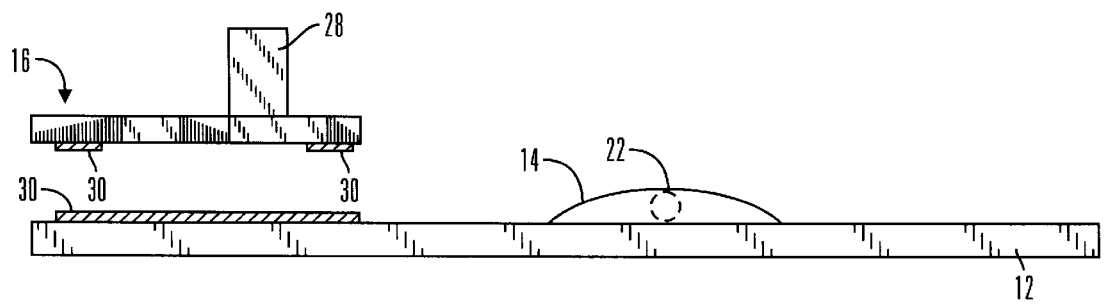
Figure 2A:
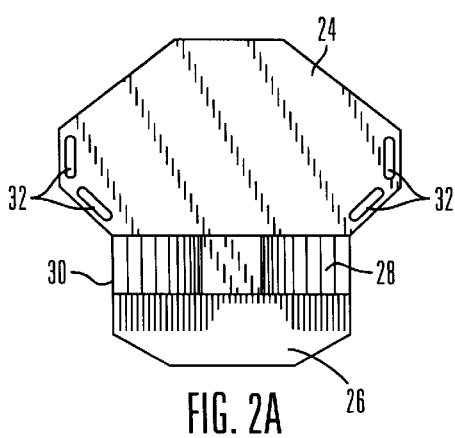
FIGS. 2a–c are top, side and end views of a detachable head rest employed with the embodiments of FIGS. 1a–b.
Figure 2B:
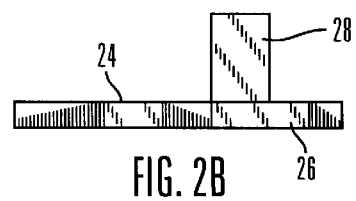
Figure 2C:
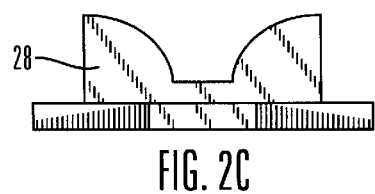
Figure 3:
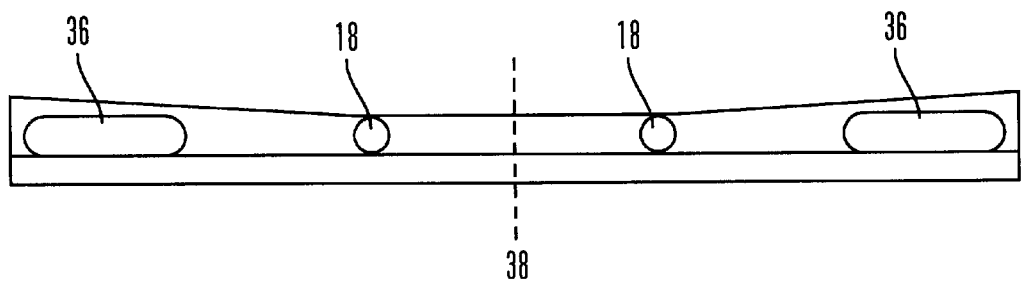
FIG. 3 is a sectional view of the lumbar pad of FIGS. 1a–b showing the location of pressure sensors and vibrator units within the pad.

Turning now to the figures, in FIGS. 1–3, a first embodiment of an apparatus 10 of the invention includes a mat 12, preferably comprised of a non-slip material, with a lumbar pad 14 and a head support 16.

Lumbar pad 14 preferably is unitary with mat 12, that is, is formed from a section of mat 12. Disposed within lumbar pad 14 are means 18 for detecting a weight applied to a surface 20 of lumbar pad 14. The weight detecting means 18 can include means such as one or more mechanical switches, one or more pressure sensors, or other means known to those skilled in the art for detecting a weight applied to a surface.

The weight detecting means 18 are connected to one or more means 22 for producing a signal. The signal means 22 are activated when the selected weight detecting means 18 detect a weight applied to the surface 20 of mat 12. Once activated, the signal means 22 produce a signal that is perceptible by a person using the inventive apparatus.

Exemplary signal means 22 include, without limitation, devices for producing a vibratory signal, such as a mechanical vibrator; devices for producing an auditory signal, such as an electronic tone generator; devices for producing a visible signal, such as a light bulb or a light-emitting diode (LED); and the like, as well as combinations of such devices. The signal means 22 can be affixed to or within the apparatus 10, for example within lumbar pad 14, or can be located externally. The detection means 18 and the signal means 22 are connected together, for example as parts of an electrical circuit, or by means such as low-power radio transmitters. Any means for enabling detection means 18 to activate signal means 22 are considered to be within the scope of the present invention.

Optionally, lumbar pad 14 can accommodate one or more lordosis inserts 14a disposed above detection means 18 in order to support users having excessive lordotic sway. Lumbar pad 14 can also optionally include a switch (not shown) for disabling signal means 22 to allow use of the apparatus without generation of a signal.

Head support 16 includes a head/neck base 24 and a cervico-thoracic support 26. A neck support 28, which optionally is adjustable in width, is disposed on head support 16 between head/neck base 24 and cervico-thoracic support 26. As illustrated in FIG. 1b, head support 16 is detachably affixed to mat 12 by attachment means 30, for example hook/loop devices such as Velcro® fasteners, snaps, etc., in order to allow selectable positioning of the head support 16, and also to allow head support 16 to be used separately if desired. In the alternative, head support 16 can be permanently affixed to mat 12.

In a preferred embodiment, head support 16 is provided with a plurality of handles 32. Handles 32 can be formed by cutting openings in base 24, for example, or can be separately formed and affixed to base 24.

If desired, mat surface 20 can be provided with graphics 34, such as a stylized representation of a human pelvis and lower backbone, in order to facilitate orientation of a user with respect to the mat surface. Illustrations of the positions of TLC pressure points and the locations of the detection means 18 are also beneficial to assist the user in properly orientation with respect to the apparatus 10.

In a preferred embodiment illustrated in FIG. 3, signal means 22 include two vibrators 36 disposed within lumbar pad 14 along either side of the longitudinal axis 38 of mat 12. Vibrators 36 are connected to detection means 18 and are activated when detection means 18 detect a weight (e.g., the weight of a user's body) applied to the surface 20 of mat 12.

Figure 6A:
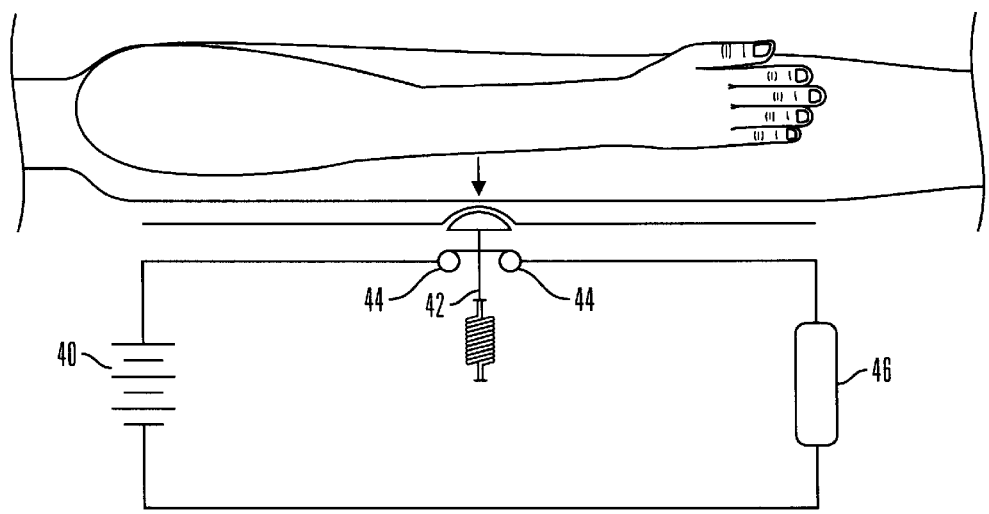
FIGS. 6a–b are schematic diagrams showing a mechanical switch useful as a pressure sensor, showing activated and inactivated states.
Figure 6B:
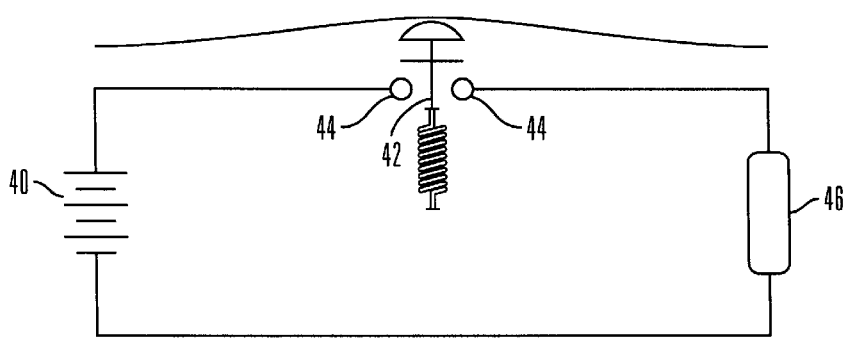

An exemple of detection means 18, illustrated in FIGS. 6a–b, include a power source 40, which can be a battery disposed, for example, within lumbar support 14 or at another location within, on or external to apparatus 10, or A/C power supplied via a plug; a mechanical switch 42 energized by a spring having a preselected spring constant; and a pair of contacts 44, which with signal means 22, such as a vibrator, form a circuit. In FIG. 6a, a weight, for example the weight of a user's body (indicated by a downward arrow), exceeds the spring force and causes the mechanical switch 42 to close, closing the circuit and activating signal means 22. Thus, when the user remains in contact with detection means 18, the circuit remains closed and the signal means 22 remains activated. When the signal means includes a vibrator unit 46 (shown in FIGS. 6a–b), the user perceives a vibratory signal applied to his back; in the alternative, when the signal means 22 includes a tone generator, light bulb, or LED, the user hears and/or sees the signal generated by the signal means 22. In any event, the user is informed when his back is in contact with the detection means 18 and exerts sufficient downward force to cause switch 42 to close.

An alternative embodiment of detection means 18 includes a pressure sensor and an associated electronic circuit in place of the mechanical switch. Such accompanying circuits are readily produced by those skilled in the art to generate an output signal in response to application of a predetermined pressure to the pressure sensor. This output signal in turn activates signal means 22. Detection means 18 can also include means for measuring the weight (or force) exerted by the thoraco-lumbar area of the user.

Figure 7:
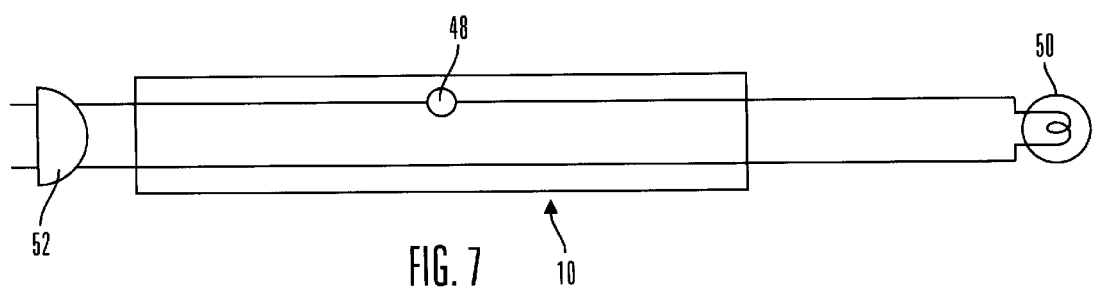
FIG. 7 is a schematic diagram of a pressure sensor with light-generating signal means and an external power supply.

FIG. 7 illustrates another embodiment of the inventive apparatus in which a pressure sensor 48 is employed rather than a mechanical switch. The signal means includes a light bulb 50. Power is supplied from an external A/C power supply via plug 52.

Optionally, a kyphosis wedge 54 is inserted between head support 16 and mat 12, to accommodate users with a head-forward position.

Figure 4A:
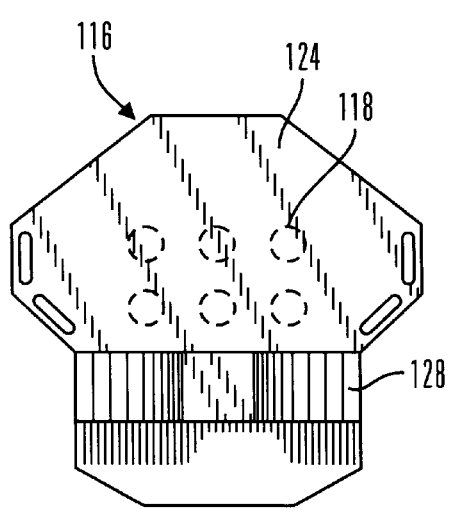
FIGS. 4a–c are top, sectional and side views of an alternative embodiment of a head rest with separate pressure sensors, vibrator units and a control switch.
Figure 4B:
Figure 4C:
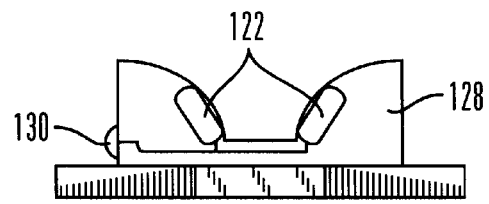
Figure 5:
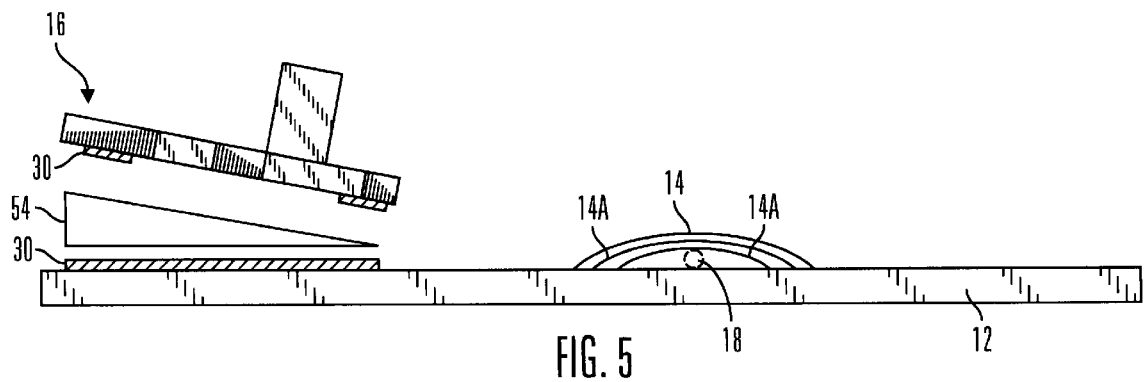
FIG. 5 is a side exploded view of an alternative embodiment including a kyphosis wedge.

FIGS. 4a–c illustrate an alternative embodiment of a head support 116 which includes detection means 118 disposed within head/neck base 124, and signal means 122. As illustrated, the signal means include vibrators disposed within neck support 128. Detection means 118 activate the signal means 122 (e.g., vibrators) when the user's head leaves contact with detection means 118. For example, when detection means 118 includes a mechanical switch, the switch is in an open position when the user's head is in contact with it, rather than in a closed position as with detection means 18 described above. When detection means 118 includes a pressure sensor, the accompanying electronic circuit produces a signal when the pressure detected falls below a predetermined level, rather than exceeding a predetermined level.

If desired, a 3-way switch 130 can be connected to detection means 118 and the vibrators. The switch 130 allows the user to selectively enable or disable the detection means 118 and to separately control activation of the vibrators. Thus, in one position, the detection means 118 are enabled to activate the vibrators as described above with respect to detection means 18 and signal means 22. In a second position, the detection means 118 are disabled, and the vibrators are deactivated. In a third position, the detection means are disabled, and the vibrators are activated, thus allowing selective user relaxation and massage while using the inventive apparatus.

Figure 8:
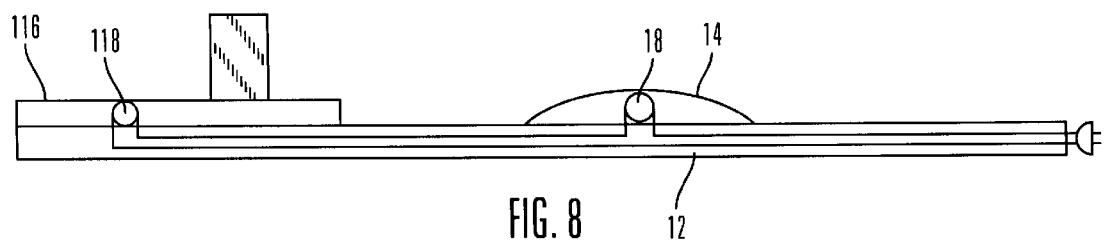
FIG. 8 is a schematic diagram of an alternative embodiment in which two pressure sensors are employed in sequence, one in the head rest and one in the lumbar pad.

The detector means 118 in the foregoing embodiment of the head support 116 can be connected in series to the detector means 18 disposed, for example, within lumbar support 14 as shown in FIG. 8. In this embodiment, the signal means 22 (and optionally vibrators disposed within head support 116) are activated only when both detector means 118 and detector means 18 detect a weight, such as the weight of a user's head and body, respectively.

The signal (vibratory, auditory, visual, etc.) provided by the inventive apparatus allows the user to heighten the intensity of muscles being worked by eliminating momentum. When in use, the signal informs the user that his thoraco-lumbar area compresses the detection means 18 sufficiently to ensure the isolation of the correct muscles usage.

The inventive apparatus preferably is used on a horizontal surface such as a floor or exercise bench. If desired, mat 12 can be provided with attachment means, such as a hook or clamp, which allows the apparatus to be affixed to a vertical surface such as a door. The apparatus can also be used on surfaces such as chairs.

The signal provided by the inventive apparatus constitutes feedback to the user while exercising, which permits the user to minimize momentum and maximize intensity. To begin exercise using the inventive apparatus in a supine position, the belt line of the user is lined up with the lumbar pad 14, and the head/neck support 16 is positioned under the user's neck where it is comfortable. If necessary, the position of the head/neck support 16 is adjusted to accommodate the user. In use, the low back is compressed into lumbar pad 14 until a signal is generated by the signal means 22. Constant tension is maintained isometrically by tightening the involved muscles.

Use of the alternative embodiment of the head/neck support 116 permits the user to avoid neck strain. If the user lifts his head during abdominal training, resulting in neck strain, the head lift is signaled to the user by the signal means 122, such as a vibration to the neck. The user can then lower his head to contact the head/neck support 116.

A progressive exercise routine designed specifically for the inventive apparatus will allow the user to start with the short (e.g., 4 minute) drill series and progress at his own pace. Precision postural positioning for strong "neutral spine" occurs when the user re-educates the neuro-muscular system using the inventive apparatus.

The invention has been illustrated herein as a self-contained apparatus. However, the invention can also be incorporated into another object, including without limitation objects such as an exercise apparatus (e.g., an inclined rowing machine), an exercise bench, a chair, a bed, etc. The invention can also be separately produced and subsequently affixed to another object.

What is claimed is:

1. A postural awareness apparatus comprising
   a) a pad having a longitudinal axis,
   b) signal means for producing a signal, said signal means comprising a plurality of vibrator units, a portion of said plurality of vibrator units being affixed to said pad at opposed locations on either side of said longitudinal axis, and
   c) detection means for detecting a weight applied to said pad and activating said signal means when said weight exceeds a predetermined weight.

2. The apparatus of claim 1 wherein said signal means produces a signal selected from the group consisting of a vibratory signal, an auditory signal and a visible signal.

3. The apparatus of claim 2 wherein said signal means comprises at least one vibrator unit.

4. The apparatus of claim 1 further comprising a head rest affixed to said pad.

5. The apparatus of claim 4 wherein said head rest is detachably affixed to said pad.

6. The apparatus of claim 5 wherein said head rest is spaced from said signal means.

7. The apparatus of claim 6 wherein said head rest is adjustably spaced from said signal means.

8. The apparatus of claim 4 wherein said head rest comprises at least one vibrator unit disposed within said head rest.

9. The apparatus of claim 8 further comprising means for activating said at least one vibrator unit disposed within said head rest independent of said detection means.

10. The apparatus of claim 4 wherein said head rest comprises a plurality of handles.

11. The apparatus of claim 4 further comprising a wedge for insertion between said head rest and said pad.

12. The apparatus of claim 1 wherein said detection means comprises a mechanical switch which closes when a weight applied thereto exceeds a predetermined pressure.

13. The apparatus of claim 12 wherein said mechanical switch comprises a spring.

14. The apparatus of claim 1 wherein said detection means comprises a pressure sensor and an electronic circuit which generates an output when pressure measured by said pressure sensor exceeds a predetermined pressure.

15. The apparatus of claim 4 wherein said detection means is spaced from said head rest.

16. The apparatus of claim 6 wherein said detection means and said signal means are affixed to said pad adjacent one another and wherein said detection means and said signal means are spaced from said head rest.

17. The apparatus of claim 1 wherein said pad has an upper surface on which graphics depicting at least a portion of a human spine and pelvis are disposed.

18. The apparatus of claim 1 further comprising a lordosis insert.

19. The apparatus of claim 1 further comprising means for attaching said pad to a horizontal or vertical surface.

20. The apparatus of claim 4 wherein said head rest comprises second detector means for detecting a weight applied to said head rest and second signal means, said second detector means activating said second signal means when said weight is below a predetermined weight.

21. The apparatus of claim 1 wherein said detection means comprises means for measuring said weight.

22. A postural awareness apparatus comprising
   a) a pad having a longitudinal axis, proximal and distal ends and an upper surface,
   b) a head rest adjustably affixed to said proximal end of said pad,
   c) signal means for producing a signal, said signal means comprising a plurality of vibrator units affixed to said pad, said vibrator units being in spaced relationship to said head rest, a portion of said plurality of vibrator units being affixed to said pad at opposed locations on either side of said longitudinal axis, and
   d) detection means for detecting a weight applied to said pad and activating said signal means when said weight exceeds a predetermined weight, said detection means and said signal means being affixed to said pad adjacent each other.

* * * * *